United States Patent [19]
Gold

[11] Patent Number: 5,829,975
[45] Date of Patent: Nov. 3, 1998

[54] ORTHODONTIC APPLIANCE

[76] Inventor: Stephen Gold, 2001 Nicasio Valley Rd., Nicasio, Calif. 94946

[21] Appl. No.: 942,002

[22] Filed: Oct. 1, 1997

[51] Int. Cl.[6] .................................................. A61C 3/00
[52] U.S. Cl. ............................................................. 433/19
[58] Field of Search ................................. 433/18, 19, 21, 433/24, 22

[56] References Cited

U.S. PATENT DOCUMENTS

| | | | |
|---|---|---|---|
| 3,798,773 | 3/1974 | Northcutt | 433/19 |
| 5,378,147 | 1/1995 | Mihailowitsch | 433/18 X |
| 5,562,445 | 10/1996 | DeVincenzo et al. | 433/18 X |
| 5,738,514 | 4/1998 | DeVincenzo et al. | 433/18 X |

*Primary Examiner*—Nicholas D. Lucchesi
*Attorney, Agent, or Firm*—Larry D. Johnson

[57] ABSTRACT

A continuous force, replaceable spring appliance which connects to the orthodontic archwires of the upper and lower jaws and teeth. The replaceable spring fits into a hollow telescoping cylinder assembly by unscrewing end caps. The spring can be made to exert a pushing force, pushing the telescoping cylinders apart as it works, or it can exert a pulling force, pulling the ends of the telescoping cylinders together. The telescoping assembly has end caps that have bars with balls attached. The balls fit into a socket assembly that is screw locked to the archwires. The ball and socket assembly allows a free range of motion, and prevents the appliance from pinching the cheeks and gums or being chewed by the teeth.

6 Claims, 3 Drawing Sheets

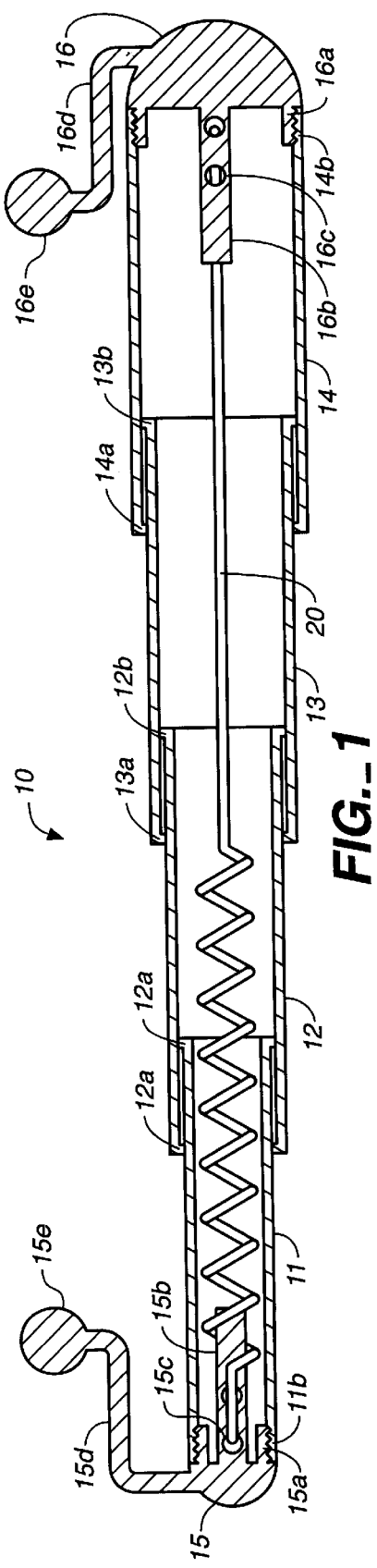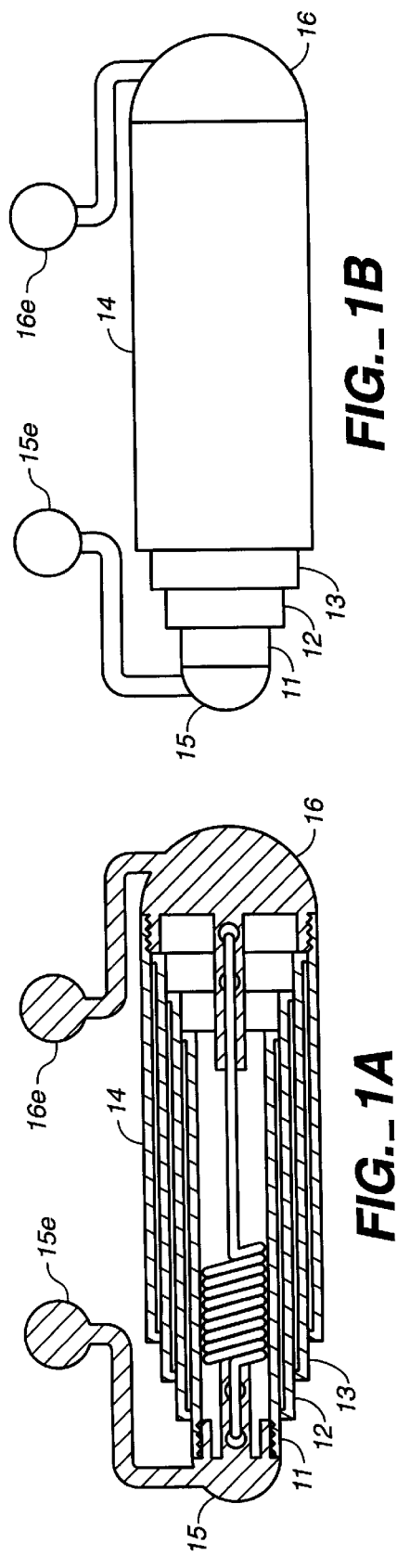
FIG._1
FIG._1A
FIG._1B

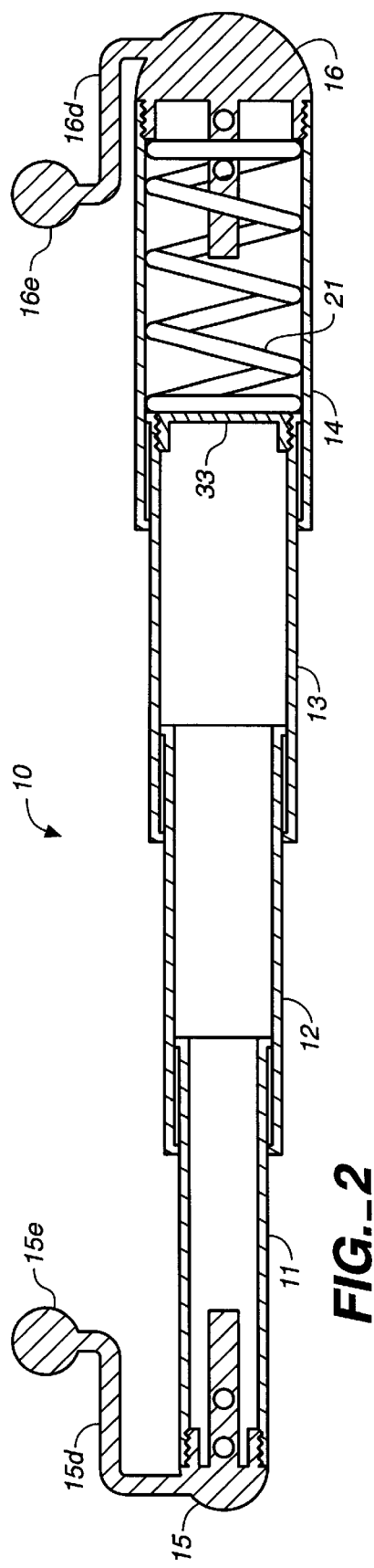
FIG._2
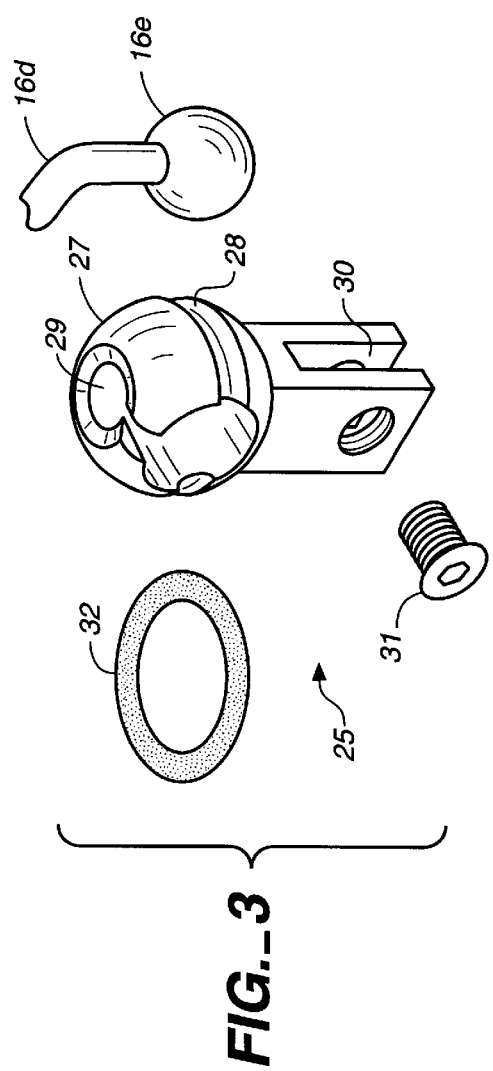
FIG._3

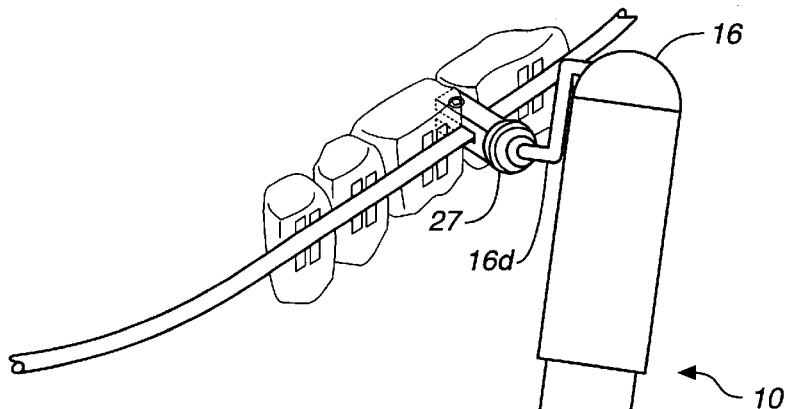
FIG._4
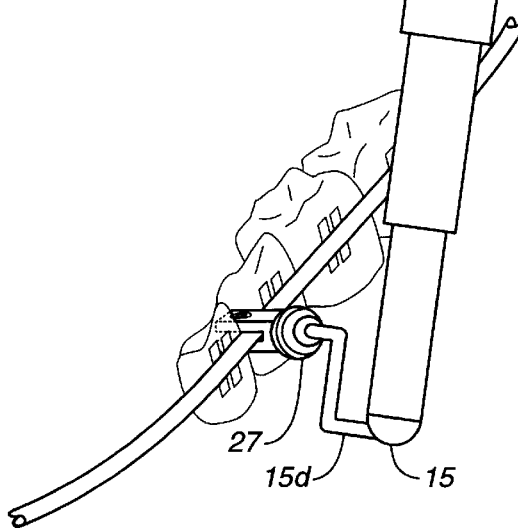
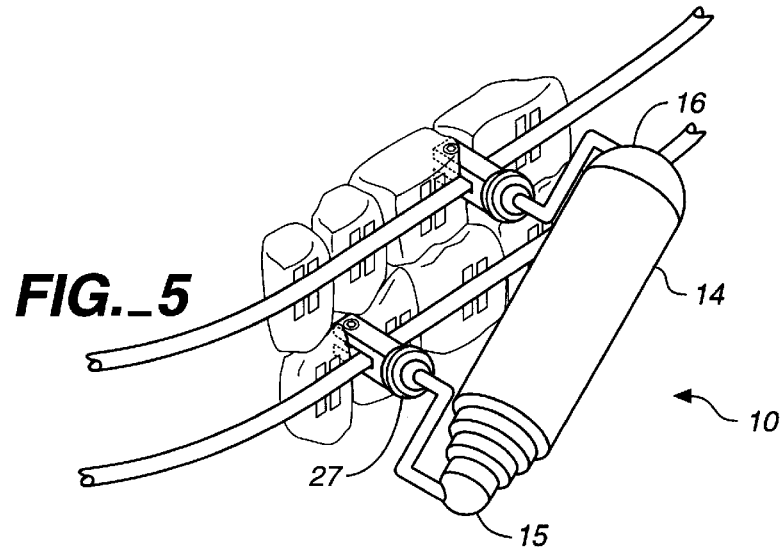
FIG._5

ORTHODONTIC APPLIANCE

BACKGROUND OF THE INVENTION

1. Field of the Invention

This invention relates generally to dental equipment and associated hardware, and more specifically to an improved orthodontic appliance.

2. Description of the Prior Art

The first appliances designed to exert a force between the upper and lower jaws were coil springs tied to the orthodontic archwires on a patient's upper and lower jaws and teeth. These springs tended to break at their attachment to the archwires, weaken and stretch, distort, collect food, pinch the cheek and gums, limit the movement of the jaws, and get crushed in the chewing action of the opposing teeth.

Jones U.S. Pat. No. 4,795,342 has a pulling spring contained within a cylinder. This did not correct the range of motion problem.

Jasper U.S. Pat. No. 4,708,646 encloses a spring in a plastic material and compressed the spring so that it exerted a force by pushing against the opposing teeth and jaws. This spring breaks at the attachments to the archwires and weakens rapidly so it has to be replaced often.

DeVincenzo et al. U.S. Pat. No. 5,562,445 discloses a spring within a telescoping cylinder. These springs break because the attachment to the archwire is free to rotate around the archwire. The appliance gets crushed by the teeth biting together. The spring often breaks or weakens and the appliance must be discarded. Appliance replacement and removal is difficult because wires have to be bent and tied. The appliance pushes against braces on the teeth and loosens the brace attachment to the teeth. The cylinders separate if the jaws are opened too far causing the appliance to become inoperable.

SUMMARY OF THE INVENTION

The present invention provides an orthodontic appliance for exerting a light continuous force between the upper and lower teeth and jaws. The inventive appliance consists of a plurality of hollow telescoping cylinders, nestled inside each other, which expand and contract by sliding over each other. The cylinders are prevented from separating by steps at their ends. The cylinder assembly expands and contracts as the patient's jaws open and close. A spring can be inserted into the telescoping cylinders by unscrewing the end caps that are threaded onto the distal ends of the innermost and outermost cylinders (i.e., the distal ends of the telescoping tubes). A replaceable spring enables the appliance to be reused after an old spring weakens or breaks. The spring is attached to end cap tie posts and made to exert a force by either pulling or pushing the ends of the cylinders apart or together. An appliance that can push or pull has a greater range of functions for moving the teeth and jaws.

The telescoping cylinders allow the jaws to open or close to their full range of motion without separating or disconnecting the appliance. The outermost cylinder end caps have inwardly (medially) bent bars which end in balls. The balls fit into archwire socket attachments that are screw locked to the orthodontic archwires of the upper and lower jaws and teeth. The balls are maintained in the socket attachment by O-rings (orthodontic alastics) that are slipped onto a groove that encircles the socket. The rigid end cap bars protrude from an opening in the socket that allows freedom of rotation. This allows the jaws to move in all directions when the cylinder assembly is attached, but prevents the appliance from being chewed on by the teeth or to impinge against the cheeks. The socket attachment is fixed to the archwire with a screw lock device. This screw locking attachment securely fastens the appliance to the archwire and prevents the accidental dislodgement of orthodontic brackets. No bending, tying or adjustment of wires is necessary to place or rewire the appliance.

The appliance can exert a pulling force similar to an orthodontic elastic, or it can exert a pushing force similar to a functional appliance such as a Herbst or Jasper Jumper.

This push/pull renewable spring appliance has the following advantages:

1. A spring that can be arranged to pull in a manner similar to orthodontic elastics, or push similar to a functional appliance such as a Jasper Jumper.

2. A spring that is replaceable after it weakens or breaks. The whole appliance does not have to be discarded.

3. The force of the spring can be varied, e.g., by changing the material from which the spring is made, or the design of the spring. This allows the appliance to exert a light elastic force, or a strong functional force.

4. The appliance protects the spring from breakage and makes replacement of a weakened spring easy by simply removing orthodontic elastics and unscrewing the end caps.

5. A fast easy insertion and removal of the appliance without tying, bending or adjusting wires. A simple hex wrench attaches the appliance to the archwires.

6. A secure attachment to the archwires which prevents the appliance from pushing against and dislodging orthodontic brackets.

7. A ball socket assembly which allows the jaws great freedom of movement while preventing the appliance from being crushed by the chewing teeth or impinging on the cheeks or gums.

8. An appliance that does not separate or come apart when the patient opens their jaws wide (rendering the appliance inoperable).

9. A sterilizable, reusable, hygienic reusable stainless steel appliance.

There is a wide market for a fixed removable appliance that provides a light continuous pulling force similar to a Class II, III elastic, or a functional pushing force similar to a Herbst or Jasper Jumper. By shortening the cylinders lengths, this appliance could also apply a vertical (intrusive) force to help close open bites.

BRIEF DESCRIPTION OF THE DRAWINGS

FIG. 1 is a side elevation cross-sectional view of an orthodontic appliance of this invention, illustrating a pulling force cylinder assembly embodiment;

FIG. 1a is a side elevation cross-sectional view of the appliance of FIG. 1 in its compressed (retracted) state;

FIG. 1b is a side elevation view of the compressed appliance;

FIG. 2 is a side elevation cross-sectional view of a pushing force cylinder assembly embodiment;

FIG. 3 is an exploded perspective view of a ball socket screwlock archwire assembly of this invention;

FIG. 4 is a perspective view of the appliance as installed on the open mouth of a patient; and FIG. 5 is a perspective view of the appliance on the closed mouth of a patient.

DETAILED DESCRIPTION OF A PREFERRED EMBODIMENT

FIG. 1 shows an orthodontic appliance 10 with four cylinders 11, 12, 13, and 14, nestled inside of each other and able to slide back and forth over each other in telescoping fashion. The inner ends of the cylinders include stops 11a, 12a/12b, 13a/13b, and 14a which prevent the cylinders from sliding apart. At the outer ends of the outer cylinders 11, 14 are threads 11b, 14b able to receive the threads 15a, 16a of the end caps 15, 16 that screw onto the outer cylinders. The inside of the end caps 15, 16 have tie posts 15b, 16b with holes 15c, 16c through them. The holes 15c, 16c are made to attach to the ends of the replaceable spring 20 which is inserted inside the hollow cylinder assembly. The end caps 15, 16 have bars 15d, 16d which end in laterally-displaced balls 15e, 16e.

When the appliance is arranged for a pulling force (FIG. 1), the spring 20 is attached to the tie posts of both endcaps so that it is stretched as the mouth is opened and the cylinders expand. The internal spring assembly can instead be made to exert a force by pushing (FIG. 2). In this case, an intermediate endcap 33 is inserted into the next to last tube 13 so that the tube acts as a piston pushing against the spring 21 that has been placed in cylinder 14. The appliance is compressed when it is placed in the mouth and the spring pushes against the end cap 33 and exerts an expanding force against the opposing teeth and jaws.

The balls 15e, 16e fit into the socket archwire assembly 25. The socket assembly 25 contains a ball socket 27 with a groove 28 encircling it, and a hole 29 from which the end cap bars 15d, 16d protrude and are able to rotate. The socket assembly also has an archwire slot 30 into which an orthodontic archwire can be secured with screw 31 and hex wrench. The groove encircling the ball socket is made to receive an O-ring (orthodontic alastic) 32 that keeps the ball in the socket as the appliance works.

The inventive apparatus thus provides a series of hollow cylinders, the number of cylinders can vary depending on the size of the mouth. The cylinders, nestled inside of each other, are able to slide over each other, similar to a telescope. The cylinders have stops so that they will not separate from each other as they are extended. A replaceable spring can be inserted into the ends of the hollow cylinders. Both ends of the spring can be tied to opposite end cap tie posts and the spring will exert a pulling force as the mouth is opened and the telescoping cylinders are extended. An end cap may be inserted into the next to last cylinder and a replaceable spring placed in the hollow cylinder so that it exerts a pushing force as the telescoping cylinders extend themselves.

End caps can be unscrewed from the outer ends of the telescoping cylinder assembly. The end caps have tie posts to connect and guide the spring that fits into the hollow ends of the cylinders. The outside of the end caps have medially-oriented bars or arms ending in balls that fit into the socket attachment.

A ball and socket assembly is secured to the orthodontic archwire by a screw locking mechanism. The ball that is attached to the removable end caps fits into the socket assembly that is attached to the orthodontic archwire. The ball and socket attachment allows freedom of movement of the jaws as the bars of the end caps rotate through a hole in the socket assembly.

The ball is held into the socket attachment by an O-ring that fits into a groove surrounding the socket. The screw lock mechanism holds the socket assembly to the archwire by tightening a screw against the archwire with a hex wrench.

While this invention has been described in connection with preferred embodiments thereof, it is obvious that modifications and changes therein may be made by those skilled in the art to which it pertains without departing from the spirit and scope of the invention. Accordingly, the scope of this invention is to be limited only by the appended claims and equivalents.

What is claimed as invention is:

1. An orthodontic appliance for attachment to the orthodontic archwires of a patient's upper and lower jaws and teeth, said orthodontic appliance comprising:

a plurality of hollow telescoping cylinders having a pair of distal ends on an innermost and outermost cylinder;

end caps removably attached to said distal ends;

spring means for exerting a spring force on said telescoping cylinders, said spring means removably attached to at least one of said end caps;

balls attached to said end caps which are releasably and pivotally connected with a pair of socket members; and means for releasable attachment of said socket members to the orthodontic archwires of the patient's upper and lower jaws and teeth.

2. The orthodontic appliance of claim 1 wherein said spring means comprises a replaceable spring extending between and exerting a pulling force between said end caps.

3. The orthodontic appliance of claim 1 further including an intermediate end cap placed on a cylinder between said innermost and outermost cylinders, and said spring means comprises a replaceable spring extending between one of said end caps and said intermediate end cap and exerting a pushing force between said end cap and said intermediate end cap.

4. The orthodontic appliance of claim 1 wherein said means for releasable attachment of said socket member to the orthodontic archwires comprises a screw inserted into an archwire slot assembly.

5. The orthodontic appliance of claim 1 wherein said balls are attached to said end caps on medially-oriented bar portions.

6. The orthodontic appliance of claim 1 wherein said balls are retained in said socket members by an O-ring.

\* \* \* \* \*